(12) United States Patent
Miau et al.

(10) Patent No.: US 8,148,596 B2
(45) Date of Patent: Apr. 3, 2012

(54) WOUND TREATMENT APPARATUS

(75) Inventors: Luo-Hwa Miau, Taipei County (TW);
Jhy-Wen Wu, Hsinchu (TW);
Nan-Kuang Yao, Taoyuan County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 377 days.

(21) Appl. No.: 12/497,607

(22) Filed: Jul. 3, 2009

(65) Prior Publication Data

US 2010/0152639 A1    Jun. 17, 2010

(30) Foreign Application Priority Data

Dec. 11, 2008    (TW) ................................ 97148147 A

(51) Int. Cl.
*A61F 13/00*      (2006.01)

(52) U.S. Cl. ........................................ 602/47; 604/304

(58) Field of Classification Search .................. 604/180, 604/304, 305, 307, 313, 26, 49, 174, 175, 604/176, 179; 602/47, 43, 42, 41, 48, 57, 602/44
See application file for complete search history.

(56) References Cited

U.S. PATENT DOCUMENTS

| | | | |
|---|---|---|---|
| 3,871,377 A | | 3/1975 | Treace |
| 4,664,662 A | * | 5/1987 | Webster .......................... 602/47 |
| 5,630,855 A | | 5/1997 | Lundback |
| 6,626,891 B2 | | 9/2003 | Ohmstede |
| 7,128,735 B2 | | 10/2006 | Weston |
| 7,273,054 B2 | | 9/2007 | Heaton et al. |
| 7,988,680 B2 | * | 8/2011 | Lockwood et al. ........... 604/313 |
| 2005/0028828 A1 | | 2/2005 | Heaton |
| 2005/0101940 A1 | * | 5/2005 | Radl et al. ..................... 604/543 |

FOREIGN PATENT DOCUMENTS

WO      0185248      11/2001
* cited by examiner

*Primary Examiner* — Patricia Bianco
*Assistant Examiner* — Tarla Patel
(74) *Attorney, Agent, or Firm* — WPAT., P.C.; Justin King

(57) ABSTRACT

A wound treatment apparatus is disclosed, which comprises: a first portion, a second portion and a porous matrix. In an exemplary embodiment of the invention, the first portion, being an adhesive film, is formed with at least a first hole; and the second portion, being made of a flexible, water-resistant material, is formed with at least a second hole and at least a third hole in a manner that the at least one second hole and the at least one third hole are capable of communicating with each other and thus causes an accommodation space to be formed inside the second portion while the at least one second hole is arranged at a position corresponding to the at least one first hole as the second portion is connected to the first portion. Moreover, the porous matrix is received inside the accommodation space of the second portion.

14 Claims, 5 Drawing Sheets

WOUND TREATMENT APPARATUS

FIELD OF THE INVENTION

The present invention relates to a wound treatment apparatus, and more particularly, to a negative pressure wound therapy (NPWT) apparatus capable of sealing a wound for facilitating a negative pressure to be applied inside the wound that not only can prevent the wound from being irritated by any tube capable of causing discomfort to the patient as no tube will be placed above the wound, but also can prevent the tubes from bending and thus clogging.

BACKGROUND OF THE INVENTION

Generally, a vacuum assisted closure (VAC) therapy or a negative pressure wound therapy (NPWT), being classified as a kind of adjuvant physical therapy, is operated by applying a negative pressure pump to a patch of a bio-compatible porous wound dressing covering a wound for forming a negative pressure inside the wound, by that, as the negative pressure will cause the volume of the porous wound dressing to contract and consequently force the wound to close as well as the shear stresses of the contracted porous wound dressing will cause a drag to the boundary tissues of the wound for enhancing cell division and proliferation, the healing of the wound can be accelerated. It is noted that the application of the negative pressure through the porous wound dressing not only can improve the growth of blood vessels and the local blood circulation as the flowing of tissue fluid between cells can be enhanced, but also it can prevent the happening of edema and inflammation, create a moist healing environment with good wound protection as it can draw cellular waste and excess tissue fluid out of the wound, and thus the healing time of the wound can be reduced.

Generally, a conventional NPWT system comprises: a patch, for covering and sealing a wound; a bio-compatible porous wound dressing, for placing inside the wound; a drainage tube, placed adjacent to or inserted in the dressing for connecting the wound to a spent liquid container; and a connection tube, connecting the spent liquid container to a vacuum source; by which a negative pressure is applied to the wound for draining spend liquid from the wound to the spent liquid container. As the negative-pressured drainage tube is directly inserted into the dressing that is placed inside the wound, there will be some components of the NPWT system to be disposed on top of the wound forming an obstructive structure. Such obstructive structure not only may adversely affect the airtightness of the wound as the patch may be deformed or even damaged by the pressing thereof, but also it may sometimes cause clogging in the drainage tube and thus affect the healing of the wound. In addition, when the wound is formed on the back or foot of a patient, such as diabetic foot lesions or bedsores, such obstructive structure may cause discomfort to the patient.

There are already some studies trying to improve the conventional NPWT system. One of which is a drainage system, disclosed in U.S. Pat. No. 6,626,891, entitled "Drainage system to be used with an open wound, an element which is used thereby for placing a drainage tube or hose and a method of using said drainage system". The aforesaid drainage system is consisted of: a block of a foamy material, placed on a wound for absorbing wound fluid; a plate-shaped member, configured with a thickening in a manner that there is a hollow space formed inside the thickening; and a foil, affixed to the upper side of plate-shaped member while capable of adhere to the skin surrounding the wound; wherein the hollow space in the thickening is enabled to communicate with the block through a plurality of opening, and is connected to a drainage tube through an open formed on the thickening while the drainage tube is connected to a suction pump. Thus, it will be apparent that the wound fluid can be withdrawn out of the wound through the foamy block, the openings formed on the plate-shaped member, the hollow space inside the thickening and the drainage tube. However, as the plate-shaped member must be formed with a specific hardness and thickness and also as the thickening and the drainage tube are placed at a position about the center of the wound, such configuration not only may adversely affect the airtightness of the wound as the foil may be easily detached from the plate-shaped member by the pressing thereof, but also it may sometimes cause clogging in the drainage tube since it can be bended easily during usage or cause the drainage tube to be pull loose by careless usage. In addition, it can cause discomfort to the patient as it is pressed directly on the wound.

Another such study is a wound therapy device disclosed in U.S. Pat. No. 7,273,054, entitled "Surgical drape and head for wound treatment". The aforesaid wound therapy device is basically a flat head having a plurality of column-like projections formed on a side thereof while having a connector formed on another side thereof in a manner that it penetrates the flat head and is provided for connecting to a suction pump through a drainage tube. By covering the side of the flat head where the column-like projections are formed on a dressing fitted inside a wound as the flat head is blanketed under a flexible film that is adhere to the skin surrounding the wound, the wound fluid can be withdrawn out of the wound through the dressing, the apertures formed between the column-like projections, the connector and the drainage tube. Similar to the device disclosed in U.S. Pat. No. 6,626,891, As the formation of the column-projections on the flat head causes the flat head must be formed with a specific hardness and thickness and also as the connector and the tube are placed at a position about the center of the wound, such configuration not only may adversely affect the airtightness of the wound as the flexible film may be easily detached from the flat head by the pressing thereof, but also it may sometimes cause clogging in the drainage tube since it can be bended easily during usage or cause the drainage tube to be pull loose by careless usage. In addition, it can cause discomfort to the patient as it is pressed directly on the wound.

One another such study is a wound therapy device disclosed in U.S. Pat. No. 7,128,735, entitled "Reduced pressure wound treatment appliance". The aforesaid wound therapy device uses a funnel-like overlay to mask a wound so that the wound fluid can be withdrawn through a drainage tube fitted inside the overlay that is connected to a suction pump. Despite of the improvement over the airtightness performance, the bulky overlay can cause great trouble and discomfort to the movement of a patient using the treatment device. In addition, the drainage tube can be clogged as it is easily being bended in usage.

From the above description, it is noted that there is in need of a NPWT apparatus without the aforesaid disadvantages of poor airtightness performance, patient discomfort and the clogging of tubes.

SUMMARY OF THE INVENTION

The present invention relates to a negative pressure wound therapy (NPWT) apparatus capable of sealing a wound for facilitating a negative pressure to be applied inside the wound for healing the same, that not only can prevent the wound from being irritated by any tube for causing discomfort as no tube will be placed above the wound, but also can prevent the tubes from bending and thus clogging.

To achieve the above object, the present invention provides a wound treatment apparatus, comprising: a first portion, being an adhesive film formed with at least a first hole; a second portion, being made of a flexible, water-resistant material and formed with an accommodation space, at least a second hole and at least a third hole; and a porous matrix, received inside the accommodation space of the second portion; wherein the at least one second hole and the at least one third hole are capable of communicating with each other while the at least one second hole is arranged at a position corresponding to the at least one first hole as the second portion is connected to the first portion.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

The present invention relates to a wound treatment apparatus that can form a hermetic environment enclosing a wound so as to apply negative pressure inside the wound for facilitate the healing of the same. That is, the hermetic environment formed by the wound treatment apparatus of the invention is connected to a suction pump for proving the negative pressure and a waste fluid collector for storing the wound fluid, It is noted that the wound treatment apparatus is also configured with fluid transportation components by that wound fluid from the wound that is withdrawn by the wound treatment apparatus can be transported to the wound fluid collector for storage.

Figure 1:
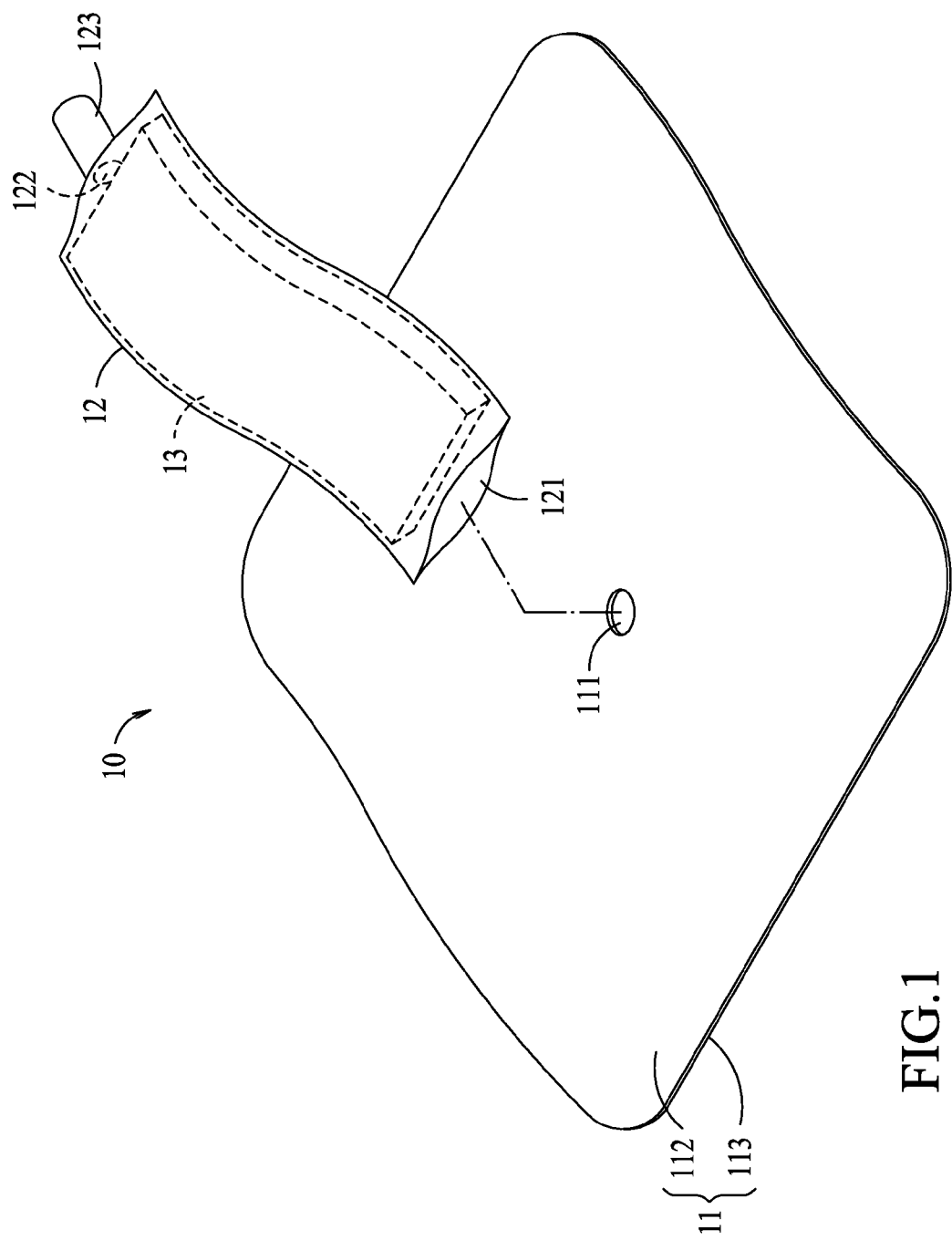
FIG. 1 is an exploded view of a wound treatment apparatus according to en embodiment of the invention.
Figure 2:
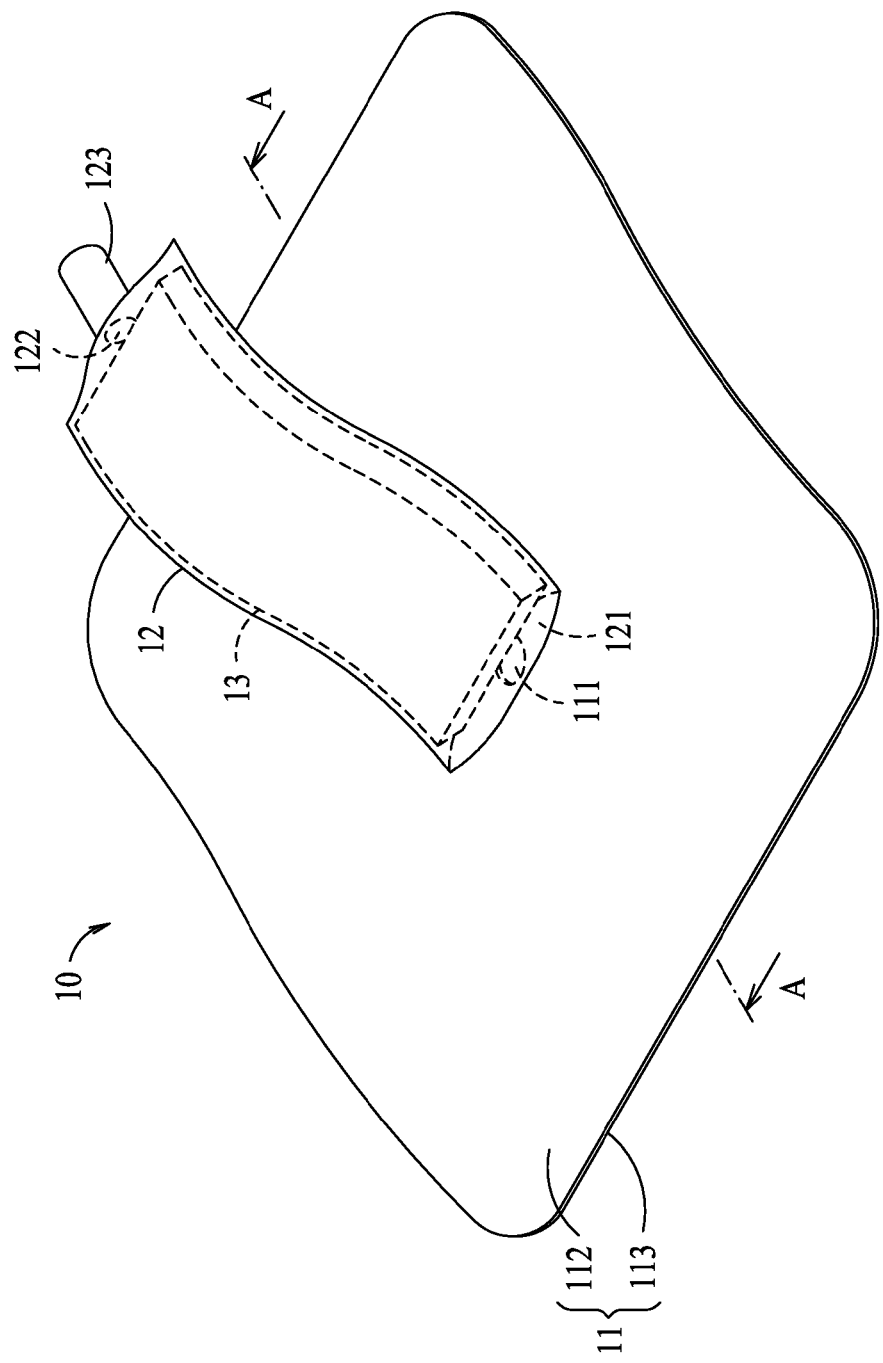
FIG. 2 is a schematic view of a wound treatment apparatus according to en embodiment of the invention.

Please refer to FIG. 1 and FIG. 2, which show a wound treatment apparatus according to an embodiment of the invention. In this embodiment, the wound treatment apparatus 10 comprises: a first portion 11, a second portion 12 and a porous matrix 13. The first portion 11 is an adhesive film, such as the transparent patch commonly known in medical community as "O.P Site", or the polyurethane (PU) film, and is configured with at least a first hole 111. The second portion 12 is made of a flexible, water-resistant material with bio-compatibility, such as polyvinyl chloride (PVC), which can be the same or different from the first portion 11. Moreover, the second portion 12 is configured with at least a second hole 121 and at least a third hole 122 in a manner that the at least one second hole 121 and the at least one third hole 122 are capable of communicating with each other and thus causes an accommodation space to be formed inside the second portion 12 for receiving the porous matrix 13. The porous matrix 13 can be made of a foamy or fibrous material such as polyurethane (PU), or polyvinyl alcohol (PVA) or any other suitable materials, or a material with reversible water absorbency, such as a gauze or a cotton thread. Nevertheless, the second portion 12 and porous matrix 13 should be made of a soft and flexible material, aperture size is ranged between 200 µm and 1500 µm. However, when the aperture size is too small, not only the efficiency of the suction pump for applying the negative pressure to the wound can be adversely affected, but also it can be easily clogged by the wastes in the wound fluid. Accordingly, the aperture size is recommended to be ranged between 400 µm and 800 µm. As shown in FIG. 2, the second portion 12 is connected to one side of the first portion 11, i.e. the top side 112, whereas the second hole 121 is disposed at a position corresponding to the first hole 111. In addition, there is an adhesive layer formed on the bottom side 113 of the first portion 11. Thereby, the second hole 121 is tightly engaged with the first hole 111 for maintaining a hermetic environment as the wound treatment apparatus 10 is in usage.

In this embodiment, the second portion 12 is formed as an elongated bag that the second hole 121 is formed at an end thereof while the third hole 122 is formed at another end. In addition, the second portion 12 is configured with a hollow tube 123 in a manner that it is extending out of the second portion 12 from the third hole 122. The hollow tube 123, being ensheathed by a joint 20, is connected to a tube 21 by that the wound treatment apparatus 10 is connected to the suction pump and the wound fluid connector. In another word, the second portion 12 is basically a component configured with unlimited amount of second holes 121 as inputs and third holes 122 as outputs that are capable of communicating with each other. It is noted that the design of the second portion 12 is not limited to that shown in this embodiment. Similarly, the first hole 111 is not limited to be shape as a circular hole, which can be formed as a rectangle or any random shape of various sizes, and can more than one first hole only if they can be used for allowing the wound fluid to flow therethrough and into the second portion 12.

Figure 3:
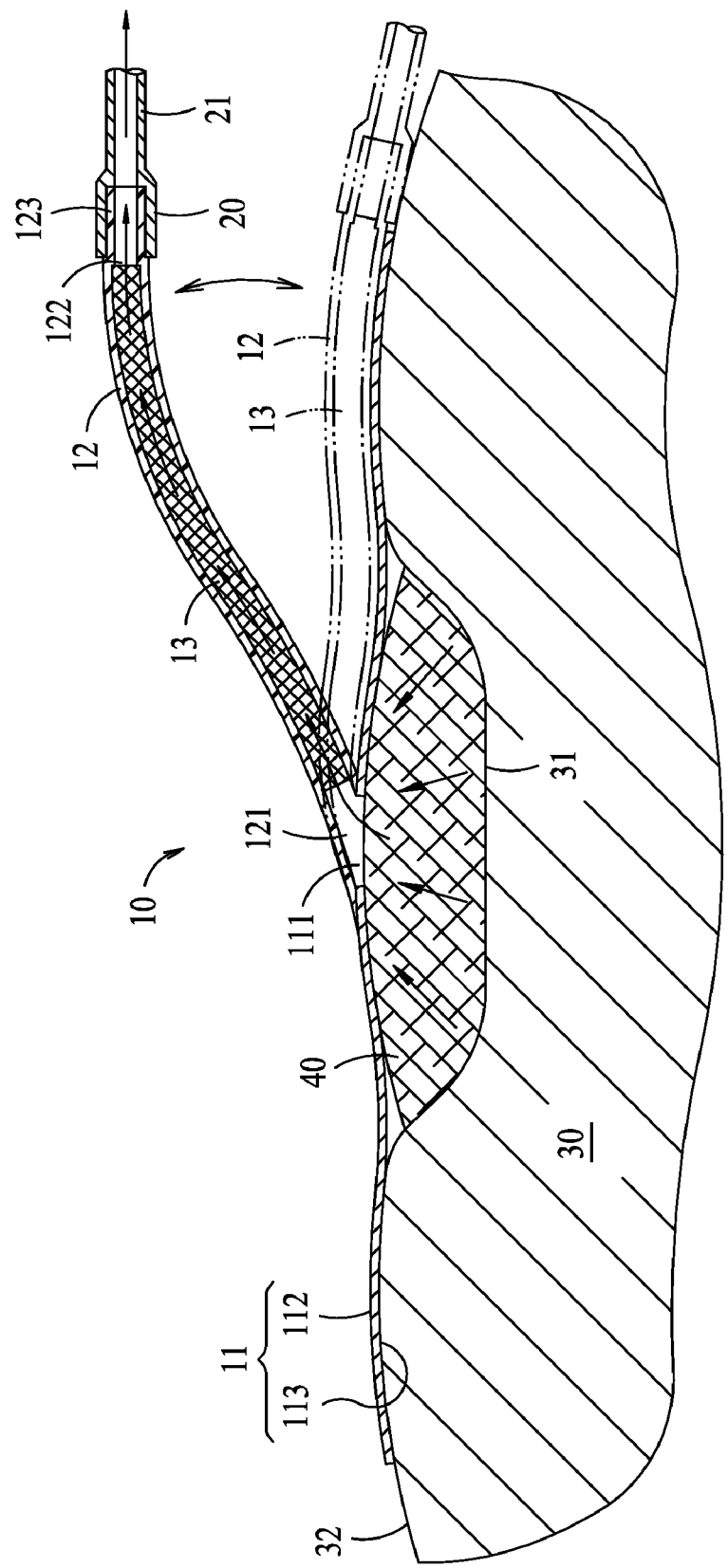
FIG. 3 is an A-A sectional view of FIG. 2 as the wound treatment apparatus is placed on a wound.

Please refer to FIG. 3, which is an A-A sectional view of FIG. 2 as the wound treatment apparatus is placed on a wound. In FIG. 3, a wound 31 of a patient 30, that is filled by a dressing 40, is covered by the first portion 11 whereas the first portion 11 is adhere to the skin 32 surrounding the wound 31 for forming a hermetic environment. Thereby, as the first hole 111 and the second hole 121 are place directly over the wound 31, the tissue fluid, blood, and other inflammation materials adsorbed by the dressing 40 can be withdrawn by the action of the negative pressure provided from the suction pump for enabling the withdrawn fluid to flow into the second portion 12 through the first and the second holes 111, 121, where it is further flow through the porous matrix 13 and then enter the tube 21 through the third hole 122 and the corresponding joint 20 and finally arrive at the waste fluid collector. It is noted that the porous matrix 13 is used for filtering the withdrawn fluid containing the tissue fluid, blood, and other inflammation materials, by that the solids containing in the withdrawn fluid can be prevented from flowing into the tube 21 and thus the clogging of the tube 21 can be prevented. Moreover, as the second portion 12 is made of a flexible, water-resistant material, the porous matrix 13 should also be made of a soft and flexible material so that it can be deformed, bended or twisted along with the second portion 12 without irritating the wound 31 when the second portion 12 is being squeezed or pressed. In addition, when the second portion 12 is deformed, bended or twisted, the porous matrix 13 fitted therein can ensure the negative pressure to be applied to the wound 31 through the apertures formed in the same, and simultaneously it can also ensure that the withdrawn fluid containing the tissue fluid, blood, and other inflammation materials can be withdrawn continuously without being stopped by the twisted second portion 12. As the tube 21 along with the joint 20 connected thereto is connected to the third hole 122 which is disposed at the outer end of the second portion 12 that is away from the first portion 11, the hard tube 21 and the joint 21 can be placed away from the wound 31 for prevent the same being irritated thereby and thus causing discomfort to the patient 30, which is especially true when the wound 31 is located at the sole or back of the patient 30.

Figure 4:
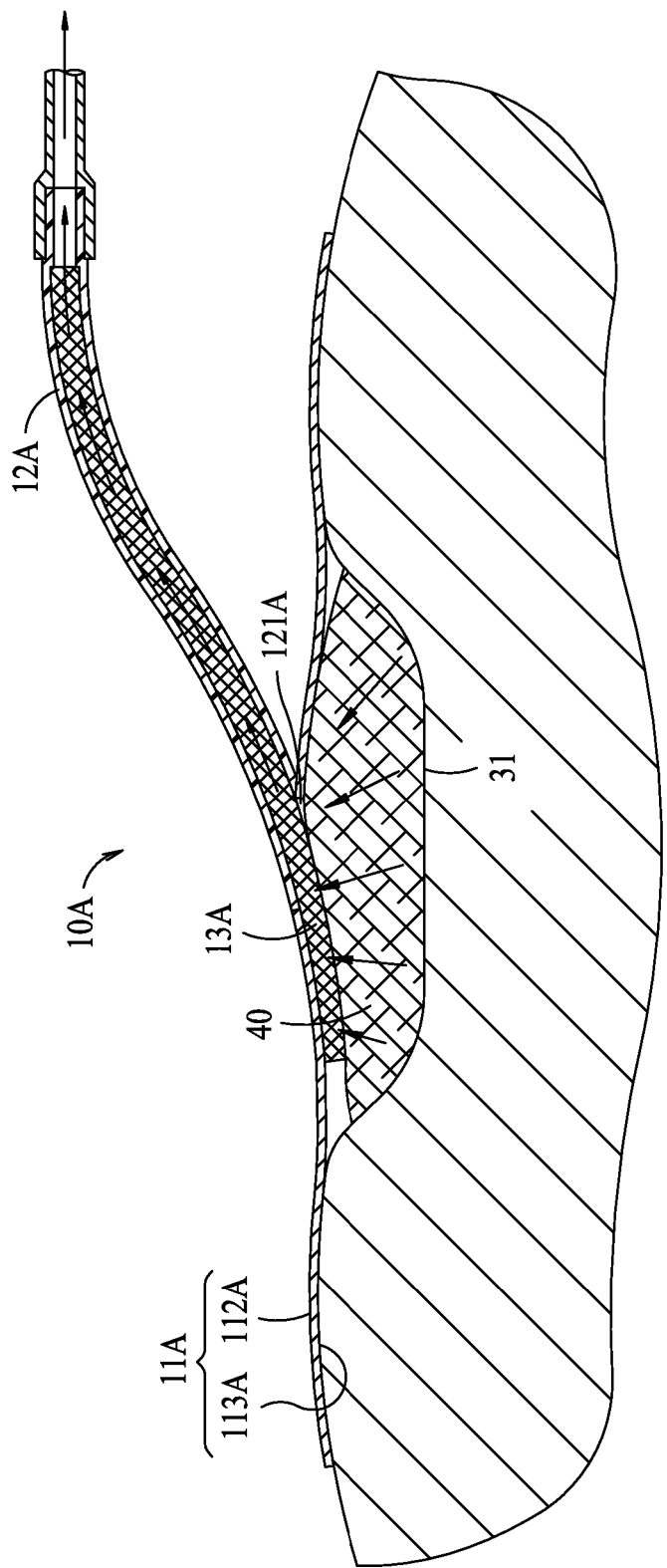
FIG. 4 is a sectional view of a wound treatment apparatus according to another embodiment of the invention as it is being placed on a wound.

Please refer to FIG. 4, which is a sectional view of a wound treatment apparatus according to another embodiment of the invention as it is being placed on a wound. The wound treatment apparatus 10A of FIG. 4 comprises a first portion 11A, a second portion 12A and a porous matrix 13A. The characteristic of the present embodiment is that: the porous matrix 13A is disposed extending out of the second portion 12A through the second hole 121A and being arranged on the bottom side 113A of the first portion 11A by a length. Thereby, when the wound treatment apparatus 10A is placed on a wound 31, the porous matrix 13A can contact directly with the dressing 40 for enabling the tissue fluid, blood, and other inflammation materials to be withdrawn in a direct and rapid manner.

Figure 5:
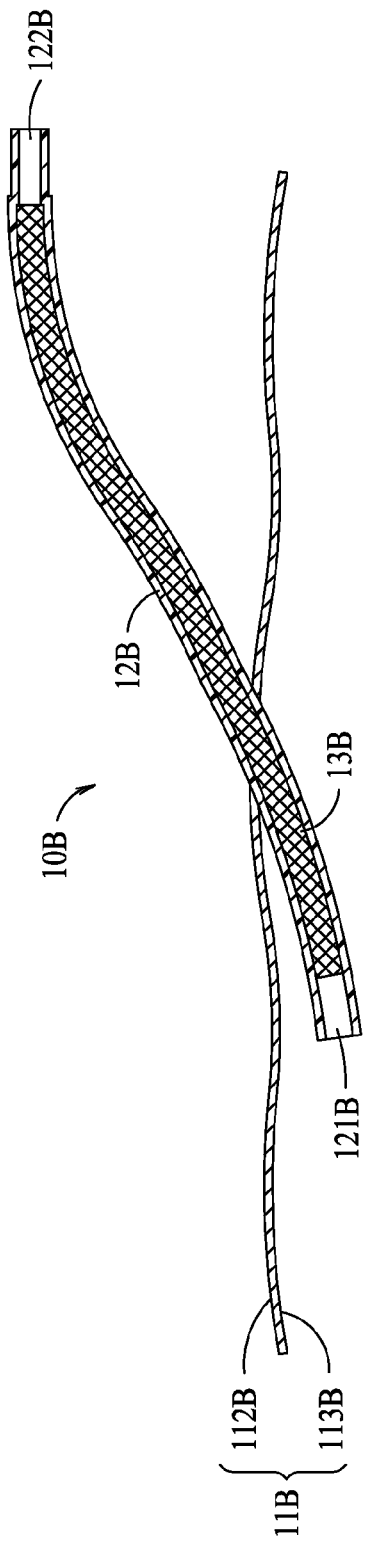
FIG. 5 and FIG. 6 are sectional views of wound treatment apparatuses according to different embodiments of the invention

In the embodiment shown in FIG. 5, the wound treat apparatus 10B comprises a first portion 11B, being an adhesive film formed with at least a first hole 111B; a second portion 12B, being made of a flexible, water-resistant material and formed with an accommodation space, at least a second hole 121B and at least a third hole 122B; and a porous matrix 13B, received inside the accommodation space of the second portion 12B; wherein the at least one second hole 121B and the at least one third hole 122B are capable of communicating with each other. The characteristic of the present embodiment is that: the second portion 12B is arranged penetrating through the first portion 11B while allowing the second hole 121B and the third hole 122B to extend out the bottom side 113B and the top side 112B of the first portion 11B in respective. Moreover, the adhesive layer is formed at the bottom side 113B of the first portion 11B.

Figure 6:
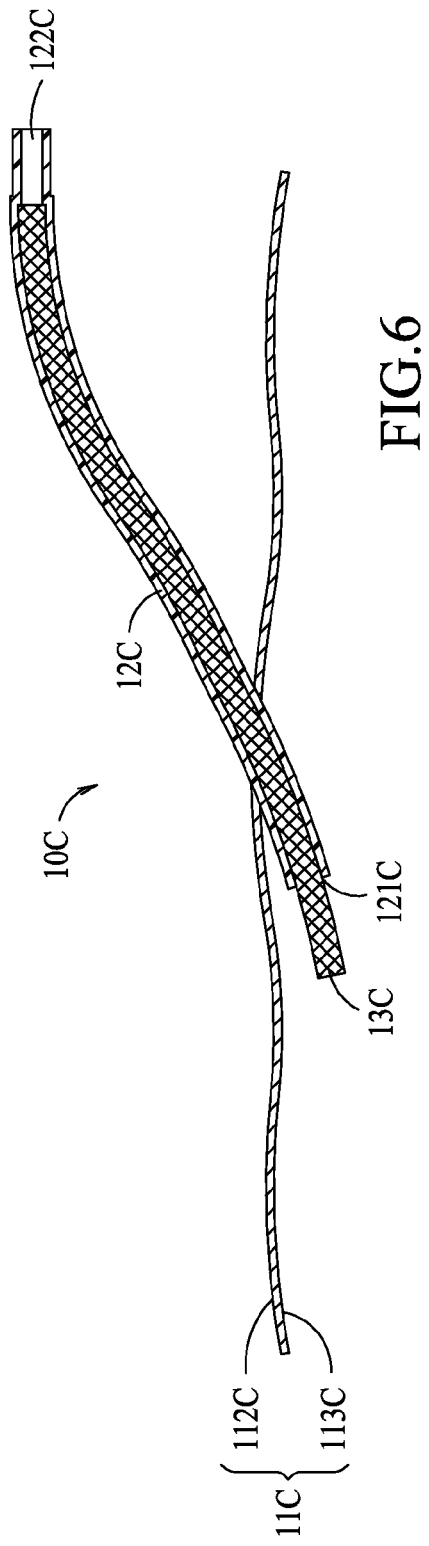

In the embodiment shown in FIG. 6 which is similar to that shown in FIG. 5, the wound treatment apparatus 11C comprises: a first portion 11C, a second portion 12C and a porous matrix 13C, in which the second portion 12C is arranged penetrating through the first portion 11C while allowing the second hole 121C and the third hole 122C of the second portion 12C to extend out the bottom side 113C and the top side 112C of the first portion 11C in respective; and the adhesive layer is formed at the bottom side 113C of the first portion 11C. The characteristic of the present embodiment is that: the porous matrix 13C is disposed extending out of the second portion 12C by a length through the second hole 121C.

To sum up, the wound treatment apparatus of the invention use its adhesive first portion to form a hermetic environment surrounding a wound while using its flexible second portion to place the joint connecting to the tube of a suction pump away from the wound, that not only can prevent the wound from being irritated by any tube capable of causing discomfort to the patient as no tube will be placed above the wound, but also can prevent the tubes from bending and thus clogging. Moreover, as the porous matrix is designed to filter the withdrawn fluid from the wound, the solids containing in the withdrawn fluid can be prevented from flowing into the tube and thus the clogging of the tube can be prevented.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A wound treatment apparatus, comprising:
   a first portion, being an adhesive film formed with at least a first hole;
   a second portion, being made of a flexible, water-resistant material and formed with an accommodation space, at least a second hole and at least a third hole; and
   a porous matrix, received inside the accommodation space of the second portion, and is disposed extending out of the second portion through the second hole and being arranged on a side of the first portion by a length;
   wherein, the at least one second hole and the at least one third hole are capable of communicating with each other while the at least one second hole is arranged at a position corresponding to the at least one first hole as the second portion is connected to the first portion.

2. The wound treatment apparatus of claim 1, wherein the first portion and the second portion are made of different materials.

3. The wound treatment apparatus of claim 1, wherein the second portion is made of polyvinyl chloride (PVC).

4. The wound treatment apparatus of clam 1, where the porous matrix is made of a foamy or fibrous material.

5. The wound treatment apparatus of claim 1, wherein the porous matrix is made of a material selected from the group consisting of polyvinyl alcohol (PVA) and polyurethane (PU).

6. The wound treatment apparatus of claim 1, wherein the porous matrix is made by a material selected from the group consisting of: a gauze and a cotton thread.

7. The wound treatment apparatus of claim 1, further comprises apertures formed in the porous matrix and at a size ranged between 200 μm and 1500 μm.

8. The wound treatment apparatus of claim 1, further comprises apertures formed in the porous matrix and at a size ranged between 400 μm and 800 μm.

9. The wound treatment apparatus of claim 1, wherein the at least one third hole of the second portion is configured with a joint.

10. The wound treatment apparatus of claim 1, wherein the second portion is formed as an elongated bag while arranging the second hole at an end thereof and the third hole at another end.

11. The wound treatment apparatus of claim 1, wherein the second portion is connected to a side of the first portion while forming an adhesive layer on another side of the first portion that is not connected to the second portion.

12. A wound treatment apparatus, comprising:

- a first portion, being an adhesive film formed with at least a first hole;
- a second portion, being made of a flexible, water-resistant material and formed with an accommodation space, at least a second hole and at least a third hole; and
- a porous matrix, received inside the accommodation space of the second portion, and is disposed extending out of the second portion by a length through the second hole;

wherein, the at least one second hole and the at least one third hole are capable of communicating with each other, and the second portion is arranged penetrating through the first portion while allowing the at least one second hole and the at least one third hole to extend out the two sides of the first portion in respective.

13. The wound treatment apparatus of claim 12, wherein there is an adhesive layer formed on one side of the first portion.

14. The wound treatment apparatus of claim 13, wherein the side of the first portion where the adhesive layer is formed on the side of the first portion provided for the second hole to extend out therefrom.

* * * * *